United States Patent [19]
Grove et al.

[11] Patent Number: 6,010,468
[45] Date of Patent: Jan. 4, 2000

[54] FOOT FLEXION DEVICE

[75] Inventors: Lucian Yates Grove, Roanoke; Richard John Freer, Richmond, both of Va.

[73] Assignee: The Discovery Group, LLC, Richmond, Va.

[21] Appl. No.: 09/035,136

[22] Filed: Mar. 5, 1998

[51] Int. Cl.[7] ........................................ A61B 5/11
[52] U.S. Cl. .................................. 601/23; 601/27
[58] Field of Search ................... 601/23, 27, 11

[56] References Cited

U.S. PATENT DOCUMENTS

| | | |
|---|---|---|
| 3,370,584 | 2/1968 | Girten . |
| 3,695,255 | 10/1972 | Rodgers et al. . |
| 4,003,374 | 1/1977 | Mizrachy . |
| 4,795,148 | 1/1989 | Rangaswamy . |
| 4,842,265 | 6/1989 | Kirk . |
| 5,112,296 | 5/1992 | Beard ........................................ 602/28 |
| 5,293,755 | 3/1994 | Thomas . |
| 5,713,370 | 2/1998 | Cook ........................................ 482/115 |
| 5,807,234 | 9/1998 | Bui et al. .................................. 600/17 |

OTHER PUBLICATIONS

Practical Electromyography, edited by E.W.Johnson, M.D. and W.S. Pease, M.D.; (Third Edition—Williams & Wilkins, pp. 1–3, 63–87.

Practical Aspects of Venous Thromboembolism Prevention An Overview, Goldhaber, Samuel Z.; CVR &R (Dec. 1994).

*Primary Examiner*—Glenn E. Richman
*Attorney, Agent, or Firm*—Venable; Gary L. Shaffer

[57] ABSTRACT

A foot dorsiflexion device comprises at least one portable boot, which can be submersed in liquids if desired, worn by a patient, having a baseplate and a footplate affixed at one end to the baseplate. An inflatable bellows is positioned between the baseplate and footplate, such that inflating the bellows moves the footplate relative to the baseplate to effect flexion of the patient's foot. A controller controls the pumping sequence of a pump which can inflate one or more boot devices. In another feature, the controller also receives information as to the patient's leg muscle activity and responds appropriately to stop/re-start the device. Such a feedback mechanism is useful to prevent flexion during an abnormal contraction pattern, such as occurs in muscle spasm or tetany. The device is can be operated remotely and in both automatic and manual modes by the user or operator.

35 Claims, 5 Drawing Sheets

FOOT DORSIFLEXION DEVICE

FOOT FLEXION DEVICE

FIELD OF THE INVENTION

The present invention is directed to a device for flexing a foot or the feet of a patient. By flexing a foot or the feet, the device stimulates circulation and exercises the muscles of the legs and feet and thereby decreases the likelihood of thrombosis and helps to maintain or increase blood and lymph circulation and ankle joint flexibility.

BACKGROUND OF THE INVENTION

A foot flexion device, when applied to the foot or feet of a patient, stimulates circulation and provides physiotherapy. Preferably, the device dorsiflexes the patient's foot or feet, that is, it rotates the foot about the ankle joint in a natural motion to thereby move the toes of the foot toward and away from the patient's knee, which in turn exercises the muscles of the foot, ankle and calf to thus achieve enhanced circulation of blood and lymph in the lower extremities and increased flexibility of the joints of the ankle and foot. By performing continuous passive flexion and extension of the muscles of the lower leg and feet, a foot flexion device provides therapy directed toward preventing both disease and atrophy in the lower extremities. Stimulation of the plantar portion of the foot can also aid in achieving these goals In foot dorsiflexion devices, the toes of the foot are moved passively in an upward-downward reciprocating motion. Foot dorsiflexion can be achieved by mechanically manipulating the sole and toe portion of the foot up/down about the natural axis of rotation of the ankle joint located at the heel of the user's foot.

Foot dorsiflexion is useful to treat individuals having decreased circulation. For example, temporarily immobilized or paralyzed persons no longer utilize the muscles of the lower leg to help pump the blood in the venous circulation back to the heart. The resultant venous blood stasis predisposes such individuals to abnormal clot formation in the legs, a condition commonly referred to as deep venous thrombosis ("DVT"). DVT is widespread, being a major complication of many surgical procedures, stroke, coma, spinal cord injury, therapeutic drug treatments and many other medical conditions. DVT is also quite common in those individuals who are bedridden or confined to wheelchairs.

Another condition which includes the symptom of blood and fluids pooling in the lower extremities is known as dependant edema. In dependant edema, otherwise healthy people experience such fluid pooling when their lower legs and feet hang for an extended period, for example, such as when they are sitting in an airplane or automobile seat, or when seated watching television. Dependant edema, which is common in people having varicose veins, can lead to DVT and all of its complications.

The repetitive contraction and relaxation of the muscles of the foot and calf as, for example, in walking, is well known to enhance blood flow. Mechanical manipulation provided by a flexion device provides similar motion to the muscles of the foot and calf and thereby prevents the pooling of blood in the venous vasculature of the lower extremities. Thus, by enhancing blood and lymph flow, the repetitive exercising or manipulation of the muscles of the foot and calf very significantly reduces the risk of DVT, a potentially lifethreatening medical condition.

Passive flexion/extension also enhances blood flow in individuals with peripheral vascular disease ("PVD"), a deteriorating condition characterized by chronically diseased or partially obstructed vasculature of the extremities. PVD has a high morbidity rate and is widespread. PVD is frequently associated with chronic alcoholism, excessive use of tobacco products, advanced diabetic states, and other diseases and conditions of the circulatory system. Gangrene and eventual amputation of all or part of an affected extremity is commonly a result of untreated or poorly treated PVD.

Thus, preventive uses of foot flexion devices include those listed above as well as, for example, preventing edema and varicosities in the surface veins in the lower extremities. Additional uses relate to surgical procedures where a patient may be immobilized for hours at a time and to other conditions where a patient's leg or legs are not being used for extended periods of time.

Traditionally, the means of improving venous blood flow or decreasing blood clotting include medications and a variety of compression devices. The uses of medications are limited, however, by systemic side effects such as uncontrolled or internal bleeding. Known compression devices include elastic compression stockings, graduated and sequential compression stockings and foot compression devices such as those made under the brand name Medi-Strumph or by the Kendall Corporation of Mansfield, Massachusetts or the Jobst Corporation of Toledo, Ohio.

Use of compression devices is cumbersome, however, since the care provider must first fit or adapt the device to the varying size and shape of the patient's limb. Furthermore, the difficulty encountered by a user in applying the devices to the limb often results in discomfort and associated decreased patient compliance. An even more serious disadvantage to such devices are the potential detrimental effects of direct compression to the arterial vasculature in patients with PVD. For these reasons, other means of preventing DVT, such as mechanical manipulators of the lower extremities, have been developed.

Mechanical devices for manipulation of the foot are well known in the exercise, medical and physical therapy fields. For example, U.S. Pat. No. 4,842,265, to Kirk discloses an apparatus for the therapeutic manipulation of a person's feet. The device of Kirk is large and cumbersome, however, and must be strapped to the foot of a bed or to a table in order to function on a patient who is substantially in a supine position. U.S. Pat. No. 3,695,255, to Rodgers et al., and U.S. Pat. No. 3,370,584 to Girten disclose devices which can produce either simultaneous or alternating dorsiflexing of a patient's feet. Devices to simultaneously manipulate the foot and massage the calf are known, as well, including U.S. Pat. No. 4,003,374, to Mizrachy and U.S. Pat. No. 4,795,148 to Rangaswamy. All of these devices suffer from one or more shortcomings, however.

For example, a foot flexion device, such as that shown in U.S. Pat. No. 4,842,265, to Kirk, disadvantageously restricts the mobility of the wearer to a lying-down position. Such a supine position is dangerous to certain patients, even when temporary in duration, since it can compromise the patient's blood and lymph circulation. Furthermore, prolonged supine positioning associated with such a device increases the incidence of bed sores, skin breakdown and necrosis. Furthermore, even where the risks of decreased arterial circulation are small, it is inconvenient for the patient to maintain a supine position. Inconvenience results in lower patient compliance and the concomitant continuation of the disease state or condition.

In addition, current foot flexion devices can be dangerous because they lack a safe way to prevent excessive or inappropriate flexion of the foot. In certain situations, such as when the patient's calf muscle goes into a spasm, tremors or tetany, or when a user voluntarily attempts to move a foot in opposition to the motion of the invention, a continuous-mode Foot flexion device can injure the muscle tissue or joints because of excessive machinegenerated flexion. Although such devices are equipped with a manual shut off, the period of time between onset of a patient's muscle spasm and the shutoff of the device by the patient is oftentimes sufficient for injury or pain to occur. Moreover, when a user of such a device is sleeping, comatose or otherwise not consciously responsive, the time between the beginning of a period of excessive or inappropriate flexion and the shutoff of the flexion device is even longer.

Thus, there is a need in the medical and health care fields for a foot flexion device which requires a minimum of attendance, is effective in all conditions requiring enhanced blood flow in the lower extremities, does not restrict patient movement, is portable, is easy to apply and use, has safety features which automatically engage to thereby prevent pain and injury to the user, and which provides controllability with respect to 1) the range or extent of flexion, 2) the rate of flexion, and 3) the amount of force applied to cause flexion. An additional need in the field is for a foot flexion device which can be used simultaneiusly in conjunction with other therapies.

SUMMARY OF THE INVENTION

It is the primary object of this invention to produce a unique foot flexion device capable of enhancing blood and lymph flow in the lower extremities of individuals to thereby decrease their risk of deep venous thrombosis, peripheral vascular disease and other conditions characterized by decreased circulation.

It is a further object of this invention to produce a foot flexion device which can be easily applied by a patient or health care provider to a patient's foot or feet.

Yet another object of this invention is to produce a foot flexion device which minimally restricts patient movement and which provides controllability with respect to the range or extent of flexion, the rate of flexion, and the amount of force applied to cause flexion of an ankle and lower leg portion in the device.

It is an object of the invention to provide a foot flexion device which can be controlled either automatically or manually by a patient using the device or by a non-patient operator, for example, a nurse or other medical attendant.

It is also an object of the invention to provide a portable, easy to use and lightweight foot flexion device, which can be submerged in warming or therapeutic fluids, if desired, to provide therapeutic benefits in addition to those afforded by the flexion action of the invention.

In accordance with these and other objects, the invention provides embodiments wherein the pausing of dorsiflexion of the patient's foot is automatically controlled by communication between one or more sensors and the controller, and also embodiments wherein the pausing is controlled by the patient using the device or by a medical attendant.

With respect to an automatically controlled embodiment of the invention, a foot flexion device for use by a patient is provided, the device comprising at least one boot comprising a calf member having a heel end and a knee end and constructed and arranged to support a calf portion of the patient's leg, a baseplate having a heel end and a toe end, wherein the calf plate and the base plate are rigidly attached to one another at their respective heel ends, a footplate having a footplate toe end and a footplate heel end, the footplate heel end being rotatably attached to the heel end of the baseplate so that the footplate may rotate with respect to the baseplate, an inflatable bellows positioned between the baseplate and the footplate such that inflation of the bellows causes rotation of the footplate relative to the baseplate to effect flexion of the patient's foot when the foot is disposed on the footplate, securing structure constructed and arranged to secure the patient's foot such that the footplate and foot move together, a pump assembly for pumping fluid to the bellows to power movement of the footplate, a controller operatively coupled to the pump assembly by at least one sensor constructed and arranged to sense and transmit a sensor signal from a muscle of the patient to the controller, wherein the controller is constructed and arranged to receive the signal and pause the pumping when the signal indicates that the muscle is contracting spontaneously or irregularly.

In accordance with other objects of the invention, an automatically controlled embodiment further comprises at least one switch operable by an operator or by the patient, wherein the switch is constructed and arranged to send a switch signal to the controller to override or preempt the signal from the sensor to thereby pause or stop the pumping. Preferably, the sensor signal is electrical and the electrical signal is at least 500 microvolts, the at least one sensor is an electromyogram lead, and the controller is electrically isolated from the patient and from the boot.

In accordance with additional objects of the invention, a foot flexion device is provided having two boots, each boot having a bellows connected to the pump. In most embodiments of the invention the fluid enters and exits the bellows by means of a tube connected between the pump and the bellows.

When operated in its automatic mode, or in automatic embodiments of the invention, the controller is preferably programed to restart from the pause following a period of electrical silence from the sensor. Typically, the electrical silence is the detection of no electrical signal greater than 100 microvolts for a period of from 1.0 to 5.0 minutes. Preferably, the controller is adjustable to restart the pumping following a period of electrical silence adjustable to be from 1.0 to 5.0 minutes.

In accordance with yet other objects of the invention, the pump assembly and the controller are adjustable to inflate and deflate the bellows at a frequency of from 0.1–20.0 cycles/minute. Also, preferably the fluid comprises one or more gasses selected from the group consisting of air, nitrogen, oxygen and carbon dioxide. Of course, the fluid can comprise one or more liquids selected from the group consisting of water, isotonic saline, saltwater and oil. Also, the fluid can comprise a mixture of one or more gasses selected from the group consisting of air, nitrogen, oxygen and carbon dioxide, and one or more liquids selected from the group consisting of water, isotonic saline, saltwater and oil.

In accordance with the safety and convenience aspects of the invention, the bellows may comprise a pressure release valve to prevent over-inflation. Also, the structure constructed and arranged to secure the patient's foot to the footplate and the patient's calf to the calf member is preferably one or more selected from the group consisting of hook and loop fasteners, straps and buckles, tensioned fabric, and at least a portion of a stocking affixed to the footplate or to the calf member. In some embodiments of the invention, the boot is constructed and arranged to allow attachment of the boot to the footrest of a wheelchair or similar assistive device.

Also, the boot may be incorporated into a receptacle or other such housing which can be placed on the floor to allow seated patients to benefit from the device. Moreover, the boot is made of appropriate materials so that it is operable while submersed in a therapeutic liquid such as water, aqueous solutions of therapeutic substances, aqueous salt solutions and therapeutic oils.

In accordance with other important objects of the invention, the boot is constructed and arranged to be disposed distal to the knee of the patient when in use, and the point of rotatable attachment of the footplate heel end to the baseplate is adjustable so that the foot flexion device may be fitted specifically to the foot of a particular patient. Also, the boot is provided with adjustable means constructed and arranged to effect dorsiflexion of the patient's foot within a set range, adjustable preferably in the range of from 1 degree to 30 degrees. Thus, the degree of dorsiflexion of the invention can be set to the needs or infirmities of a particular patient.

In accordance with other objects of the invention, the controller is adjustable to operate within a range of inputs from the at least one sensor. Also, the controller is preferably powered by a battery and the pump is powered by alternating current provided at a voltage between 100 and 250 volts. Of course, both the controller and pump can be powered by batteries.

Additional aspects of the invention include means for stimulating the plantar area of the foot of the patient wherein the means for stimulating the plantar area is constructed and arranged so that it operates either or both when the footplate is fixed with respect to the baseplate or when the footplate is disposed to rotate with respect to the baseplate. Means for stimulating the plantar area include a plantar aperture in the footplate constructed and arranged so that, during inflation, a portion of the bellows protrudes through the aperture to effect stimulation of the plantar area of the patient's foot. Another means for stimulating the plantar area is wherein the plantar aperture in the footplate is provided with a roller plate so constructed and arranged that, during inflation, a portion of the bellows displaces the roller plate through the aperture to effect stimulation of the plantar area of the patient's foot.

In some preferred embodiments, the pausing or stopping of flexion of the invention is controlled by the patient using the device or by a medical attendant. In these embodiments of the invention, a foot flexion device for use by a patient, and to be controlled by the patient or a medical attendant, comprises at least one boot comprising a calf member having a heel end and a knee end and constructed and arranged to support a calf portion of the patient's leg, a baseplate having a heel end and a toe end, wherein the calf plate and the base plate are rigidly attached to one another at the heel ends, a footplate having a footplate toe end and a footplate heel end, the footplate heel end being rotatably attached to the heel end of the baseplate so that the footplate may rotate with respect to the baseplate, an inflatable bellows positioned between the baseplate and the footplate such that inflation of the bellows causes rotation of the footplate relative to the baseplate to effect flexion of the patient's foot when the foot is disposed on the footplate, securing structure constructed and arranged to secure the patient's foot such that the footplate and foot move together, a pump assembly for pumping fluid to the bellows to power movement of the footplate, a controller operatively coupled to the pump assembly by at least one switch constructed and arranged to be operable by an operator to send a signal to the controller, wherein the controller is constructed and arranged to receive the signal and pause or stop the pumping when the signal is received.

An additional advantage of the invention is that, in most preferred embodiments, the pump assembly and the controller are connected to the boot only by the fluid tube so that the boot is physically and electrically isolated from the pump assembly and controller. In such a configuration, the patient is further protected from electrical shock which could possibly originate from a controller or other electrical component of a conventional flexion device. A similar advantage is found in the aspect of the invention wherein the controller can be operated by wireless remote control means. @@@@@@@

The timed, intermittent fluid flow into and out of the bellows results in upward pressure on the footplate and subsequent dorsiflexion and relaxation of the user's foot to a neutral position. In most people, the "neutral position" is when the plantar surface of the foot is approximately at a right angle to the longitudinal axis of the lower leg. Accordingly, the base plate and calf member of the present invention meet at an angle of approximately 110 degrees, which allows for the bulge of the calf musculature while still maintaining the right angle relationship between the plantar surface of the foot and the longitudinal axis of the lower leg.

In accordance with the preferred embodiments, intermittent pumping of fluid at pre-selected intervals (1–20 cycles/minute) results in the rapid inflation and deflation (<1 sec @ 0.2 cfm) of the bellows resulting in dorsiflexion and relaxation of the foot sufficient to exercise the joints and musculature of the leg and foot to thereby enhance blood flow. Changeover from pumping one boot to two boots can be effected by a simple rotary selector valve on the same control unit.

In accordance with another feature of the preferred embodiments, one or more standard electromyograph ("EMG") electrodes and leads are attached to the user's calf area. Electrical outputs from the EMG leads are fed into the control unit to thereby detect spontaneous muscle activity, or spasms, which may occur, for example, in unconscious patients or in those suffering from spinal cord injuries, or when a user voluntarily opposes the motion of the footplate. Upon detecting a threshold level of electrical activity a predetermined amount above background levels, the control unit pauses movement of the footplate to thereby prevent pain and injury to the user.

Typically, background electrical levels detectable from skin over resting muscle are in the range of from 0.0 to 500.0 microvolts ("$\mu V$"). In contrast, electrical levels detectable from skin over active or flexing muscle are in the range of from 1,800.0 to 4,000.0 $\mu V$, and are typically around 3,000.0 $\mu V$. Because of the differences in these ranges, an adjustable threshold for deactuating a device according to the invention is typically set between 500.0 and 2,000.0 $\mu V$.

Thus, for example, when the threshold is set at 1,000.0 $\mu V$, a spasming calf muscle which transmits an output "spike" in excess of 1,000.0 $\mu V$ through the EMG lead will cause the device to pause. Pausing occurs when, in response to an EMG output spike, the control unit interrupts the pump sequence by shutting off electrical power to the pump, thereby pausing the pumping cycle for a pre-determined period of time, typically 60 seconds, or until the device is re-actuated by the user or an operator such as a medical attendant.

The controller is programmed to re-start the pumping, preferably after receiving no input above the predetermined threshold of electromyelographic activity for about 1 minute or more. In other words, electromyelographic activity below the threshold is "silence." Preferably, the controller also is programmed to indicate prolonged spontaneous muscle activity (>1 minute) by emitting a beep or other alarm signal. Other objects, advantages and novel features of this invention will become obvious from the description and drawings that accompany this application.

When a device according to the invention is powered by an electrical source which provides power to the pump and detection systems, it has three modes, an "actuated" mode, a "de-actuated" mode, and a "shut-down" mode. When the device is "actuated," the bellows is operatively connected to a fluid source, such as an air pump, by way of a three-way valve which directs air from the pump either to the bellows to inflate it, or away from the bellows thereby allowing the bellows to deflate through an exhaust valve open to the atmosphere. Thus, when the device is actuated, the base plate is in motion except for brief periods of time at the end of each inflation period and, depending upon the frequency of activation, for varying periods of time at the end of each deflation period.

When a device according to the invention is "de-actuated," the input of fluid into the bellows is stopped and the footplate is not in motion, either because the bellows is not receiving fluid from a source such as an air pump, or because another safety feature is engaged to either prevent motion of the base plate or to deflate the bellows to thereby return it to the neutral position. Thus, by de-actuating the device, the relative motion of the foot plate with respect to the base plate and calf member stops. Preferably, upon deactuation, the bellows deflates thereby permitting the base plate to return to the neutral position.

Control systems according to the invention are generally separated into two sub-systems, a main control sub-system and a feedback sub-system. An embodiment of one control system according to the present invention is shown in FIGS. 1, 8 and 9, where the main control sub-system comprises an air pump, a 3-way valve, a valve controller, a fluid bellows for air or liquids, and a pulse generator.

During operation of the invention, the air pump provides air to the 3-way valve which in turn delivers the air either to the bellows or to the outside atmosphere. Thus, the valve has two positions, a first position where Gate A is open to thereby deliver air to the bellows and Gate B is closed, and a second position where Gate A is closed, thereby preventing the flow of air into the bellows, and where Gate B is open thereby exhausting air from the bellows to deflate it and exhausting air from the pump.

When a device according to the invention is actuated, gates A and B of the three-way valve are operatively connected so that one gate is open when the second gate is closed. For example, during the inflation phase of the actuated cycle, when gate A is open, gate B is closed thereby supplying air or other fluid to the connected bellows and preventing exhaustion of air from the bellows. During the deflation phase of the actuated cycle, when gate A is closed, gate B is open thereby preventing the input of fluid to the connected bellows and providing a path for the exhaustion of air from the bellows. Because of the weight of the footplate and the pressure of the user's foot, the bellows returns to a substantially neutral position.

Any type of valving means can be used in the invention, so long as the valving means provides a way for air to be provided from the pump to the bellows of the invention and for the air to be exhausted from the bellows when desired in accordance with the control system and in accordance with other salient aspects of the invention. Two common types of valves suitable for use in the invention are mechanically-controlled pneumatic valves and electronic valves. For example, a mechanically-controlled valve suitable for use with the invention is a Model MJV-3 pneumatic valve manufactured by the Clippard Instrument Laboratory, Inc. of Cincinnati, Ohio. The MJV-3 valve typically handles air flow in the range of from 18 to 25 cubic feet/minute ("cfm") at 100 pounds per square inch ("PSI")

Electronic valving means suitable for practicing the present invention are, for example, the combination of a Model ET-3M 3-way electronic valve and a Model 2021 high flow valve, both of which are manufactured by the Clippard Instrument Laboratory, Inc. of Cincinnati, Ohio. Air flow through an ET-3M valve is about 0.5 cfm at 50 PSI. However, when the ET-3M and 2021 valves are combined in series, air flow through the valving means is in the range of 0.10–25.0 cfm. Typically, with an air pump known in the art, such as for example a DeVilbiss Model JB2N065J, air flow out of the pump is approximately 0.3 cfm.

In operation, the pulse generator generates a control pulse of approximately 1 to 2 seconds. The pulse goes through a gate to the valve controller to trigger the valve controller to provide a signal to open the valve. In one preferred embodiment of the invention the gate is controlled by a signal from a flip-flop monostable circuit in the feedback subsystem. The flip-flop monostable circuit is the equivalent of an on/off switch which may be turned off by an EMG signal above a pre-set threshold, thereby de-actuating the device. A threshold according to the invention is based on physiological parameters for muscle and skin electrical activity and is typically 500.0 microvolts or greater. After a period of time wherein no electrical activity above the threshold level is detected, typically 120 seconds, the monostable flip-flop circuit is re-set to the "on"position thereby powering the fluid pump and reactuating the device.

When the device is actuated, the gate is open and no interrupt signal issues from the feedback subsystem and each pulse from the pulse generator causes the valve controller to control the valving means to direct air to the bellows for a sufficient amount of time, and at a sufficient pressure, to inflate the bellows to the extent desired. An inflation period is typically from 0.5–5.0 seconds although a faster or slower rate may be achieved by adjustment of the controls of the invention. After inflation of the bellows to the desired extent is completed, the valving means permits air to escape from the bellows for a sufficient amount of time to deflate the bellows, thus permitting the foot plate to return to the neutral position.

The valve is controlled by a valve controller circuit which directs air to the bellows or to an exhaust port in accordance with a signal from a monostable flip-flop circuit of a type common in the controller art. In operation, the pulse generator generates a control pulse to the valve controller circuit to direct the controller to open the valve and thereby inflate the bellows and lift the footplate. When the valve opens, air flows into the bellows to inflate it and thereby lift the footplate. Pulse frequency is adjustable, preferably to be within the range of from 1 cycle/minute to 9 cycles/minute in the case of invalids and more rapid as needed in cases, for example of physical therapy or directed exercise.

The feedback sub-system according to the invention provides a signal or impetus which interrupts the cycling of the invention so that air is exhausted immediately from the bellows, thus permitting the footplate to return to its resting position. One feedback sub-system comprises at least one EMG electrode. Typical electronic components suitable for practicing the invention, such as the triggering circuit, monostable flip-flop circuit, time base signal generator and counter and alarm circuit are avaiable, for example, from Motorola. A counter circuit useful in this subsystem of the invention would be, for example, the Motorola model mct-2132.

A feedback subsystem according to an embodiment of the invention employing an EMG is provided in accordance with physiological parameters known in the art. For example, an electrical output over 50.0 microvolts would not be detected by an EMG attached to the skin over a human calf muscle at rest or under passive movement, that is, when the ankle is being dorsiflexed without physiomotor resistance from the calf. However, when the same calf muscle is under active exercise, that is, is being moved by the patient, or is in spasm or tetany, typical electrical output detected by an EMG would be 0.5 to 5.0 millivolts, a ten-fold increase or spike in the EMG signal to the signal amplifier. Advantageously, the amount of resistance against which the foot plate operates can be adjusted to the individual user so that exceeding the resistance threshold de-actuates the device.

DETAILED DESCRIPTION OF THE PREFERRED EMBODIMENTS

Figure 1:
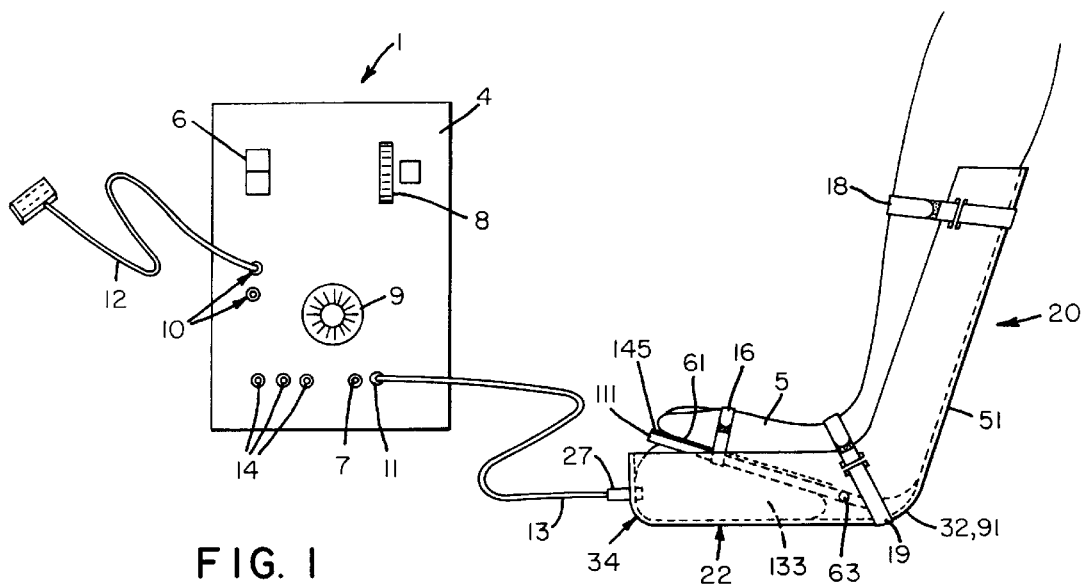
FIG. 1 is a front view of a control subsystem and a side view of a boot subsystem of the invention connected to one another by an air line.
Figure 2:
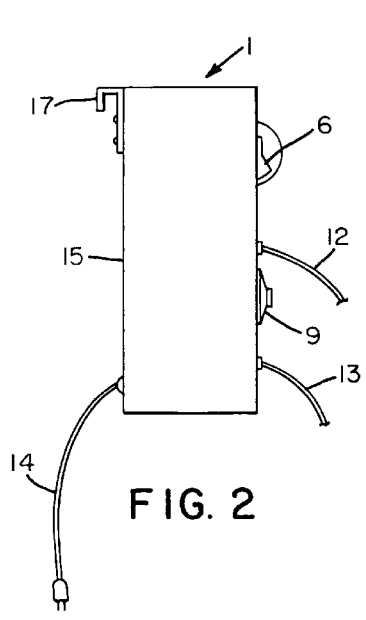
FIG. 2 is a side view of the control subsystem shown in FIG. 1.

In FIGS. 1–9, preferred embodiments of the foot flexion device according to the invention are shown with controller 1 and boot 20 connected by a length of flexible, thick walled plastic tubing 13 suitable for rapidly transmitting air or other fluids at pressures at least up to 20 lbs./square inch ("psi"). Controller face plate 4 contains an on/off switch 6, a thumbwheel dial 8 to set the rate of pumping, jacks 10 to accept electrical input from one or more standard electromyograph leads 12, and indicator lights 14 for indicating the status of the device. For example, in some embodiments of the device, four indicator lights 14 are provided. One of the four lights 14 is for indicating whether the device as a whole is receiving electrical power input from batteries or from 110 volt a.c. current, one light is for indicating that the boot is actuated, one light for indicating that the boot is paused, and one light is for indicating that electrical power to the pump is shut off due to, for example, the detection of a number of spastic events within a pre-set time period.

Dial 9 permits an operator to select use of one or two pump outlets 7, 11. Controller rear plate 15 contains power cord 14 and an optional mounting bracket 17 so that the controller may be mounted temporarily on a chair, wheelchair or bedside, for example. In some embodiments of the invention, the device is powered by batteries, such as, for example, 12 volt or 24 volt rechargeable batteries (not shown) thereby eliminating the need for a 110 volt a.c. power cord and thus decreasing the risk of shock to a user or operator.

Boot 20, which is preferably made of a moldable plastic which is rigid in its final shape, such as polypropylene, or ethylene vinyl acetate sold under the brand name Elvax, comprises rigid baseplate 22, having frontpiece 25, left raised side 26 and right raised side 28, which altogether form bellows chamber 33 for inflatable bellows 133. Rigid baseplate 22 has baseplate toe end 34 which includes frontpiece 25, and baseplate heel end 32. Baseplate heel end 32 joins calf member 51 at calf member heel end 91. Left raised side 26 and right raised side 28 of rigid baseplate 22 are constructed and arranged to provide pivot slot 65 for adjustable footplate pivot axle 63. The relative position of footplate 61 with respect to base plate 22 and calf member 51 can be set by adjusting the position of pivot axle 63 in pivot slot 65 to thereby adapt the invention to the feet and calf of a particular user.

Figure 7:
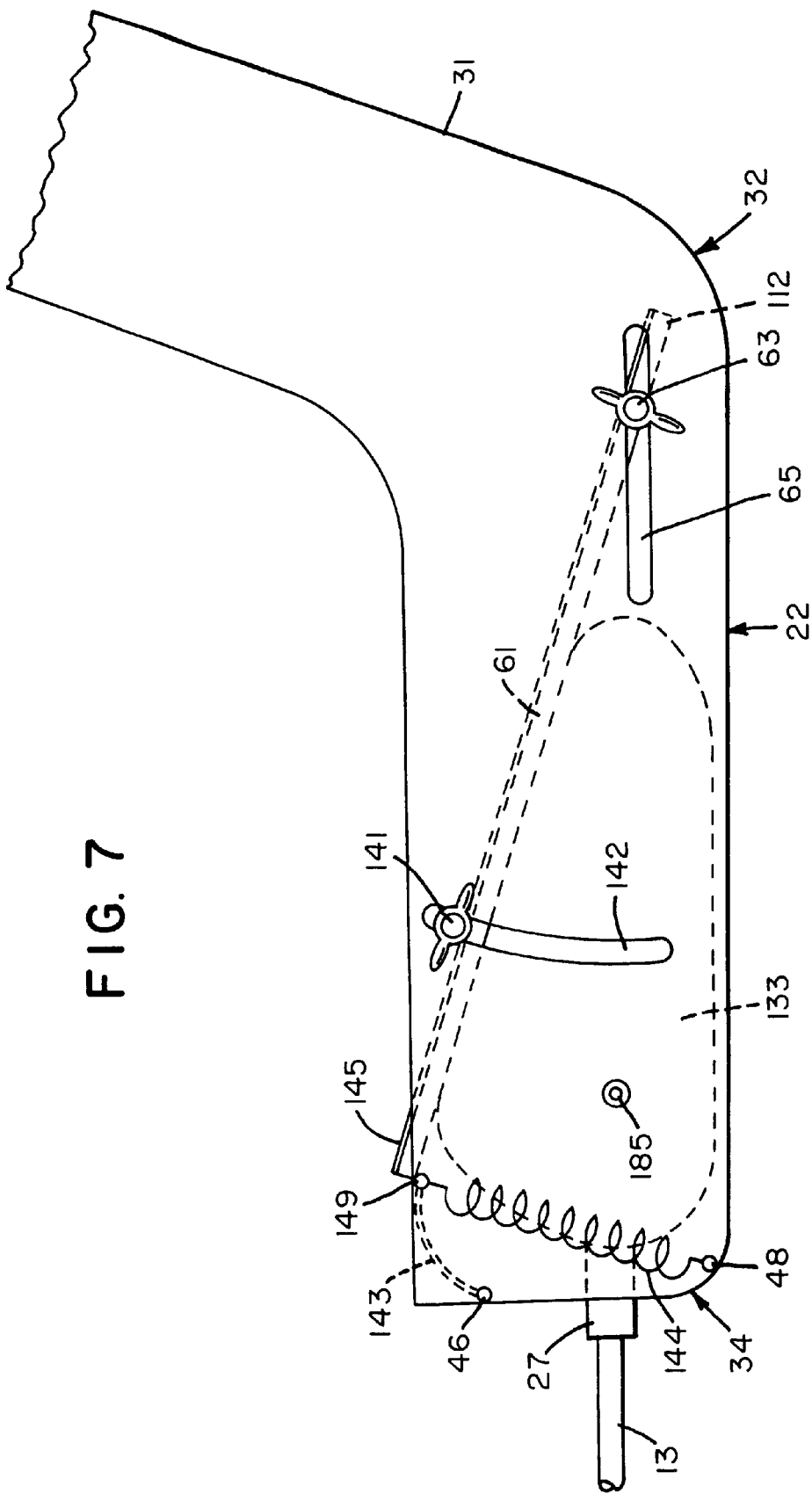
FIG. 7 is side view of the lower portion of a boot according to the invention showing features useful for adjusting and controlling the relative movement of the footplate with respect to the baseplate and calf plate.

In some embodiments of the invention, means are provided for limiting the upward travel of footplate 61 so that the risk of injury due to excessive travel of the footplate is diminished. Preferably, at least one such means is provided although more than one means may be provided depending on the specific configuration of the invention that is desired to fulfill a particular set of conditions. As is shown in FIG. 7, rigid baseplate 22 is provided with frontpiece 25 having frontpiece cable anchor 146 for attaching footplate safety cable 143 between frontpiece 25 and footplate 61 at attachment point 149 on toe end 111 of footplate 61. In other embodiments of the invention, rigid baseplate 22 is provided with shielded return spring 144, attached between spring mount 48 of baseplate 21 and spring mount 149 on footplate 61. In embodiments of the invention having both a return spring and a safety cable, safety cable 143 preferably resides within shielded return spring 144.

Figure 6:
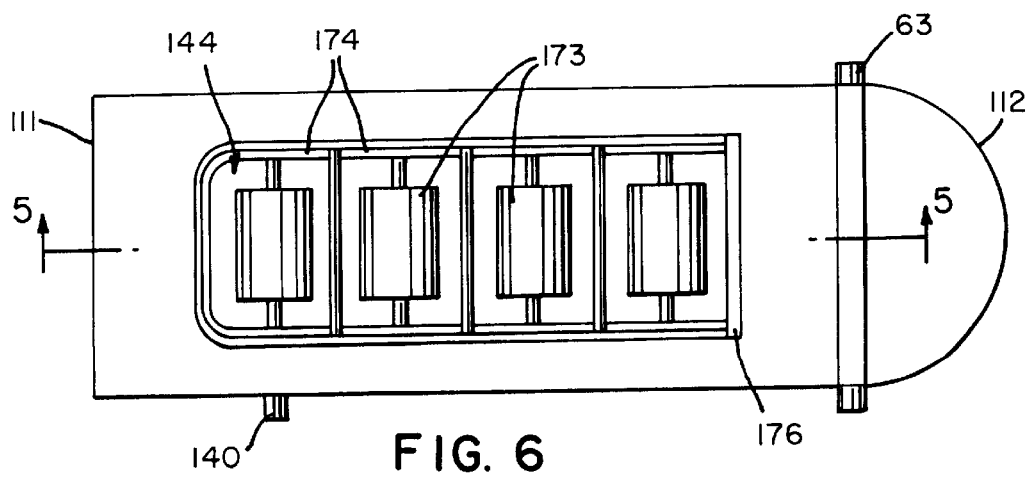
FIG. 6 is a top view of the foot plate embodiment show in FIG. 5.

The travel of footplate 61 can be limited by other means. For example, as is shown in FIGS. 6 and 7, in some embodiments of the invention, footplate 61 is provided with footplate stop tab 140 which is constructed and arranged to travel within arcuate stop slot 142 provided in raised left side 26 of base plate 21. The maximum upward travel of footplate 61 is determined by the position of adjustable stop nut 141 which is adjustably disposed within arcuate stop slot 142 and above stop tab 140 so as to engage stop tab 140 when footplate 61 is raised by bellows 133.

Preferably, boot 20 has a relatively smooth exterior 31 with heel end 32 of baseplate 22 joined to calf member 51 at calf member heel end 91 to form boot 20. Boot 20 is provided with pivot slots 65 in raised left side 26 and raised right side 28 of base plate 22. The ends of adjustable pivot axle 63 of footplate 61 are disposed within pivot slots 65. Calf member 51 extends upwardly from heel end 91 to knee end 93 of calf member 51 to provide support for the calf of a user and to hold the calf in a desired relationship to the components of the invention.

Preferably, calf member 51 joins baseplate 22 at an angle between 90 and 125 degrees, and, more preferably, about 110 degrees relative to baseplate 22. Baseplate 22 extends heelward toward pivot 63, and joins calf member 51 which extends upward from baseplate 22 approximately 5–6 inches above the ankle to approximately 12 inches above the ankle, depending on the size and needs of the user. Baseplate 22 has left raised side 26 and right raised side 28 and frontpiece 25 which form bellows chamber 33. Vertical slot 19 is positioned in frontpiece 25 from the top downward a sufficient distance to allow access for connector 27 and fluid tube 13. In some embodiments of the invention, calf member 51 and footplate 61 are secured to the foot and leg by straps 16, 18 and 19, which are provided with hook-and-loop fasteners, at the level of the ankle and just below the top of calf member 51.

Moveable footplate 61 rotatably connects to boot 20 at adjustable pivot 63. Footplate 61 is provided with padded surface 23 for the comfort of the user. In some embodiments of the invention, the user's foot is secured to footplate 61 by strap 16 which is provided with hook-and-loop fasteners just over the ball of the foot. Bellows 133 resides in bellows chamber 33, and is provided with tubing connector 27 which extends out through the slot 19 in frontpiece 25 and connects to plastic fluid tube 13. Fluid tube 13 is attached to a pump in controller 1. Bellows 133 can be secured, if needed, to rigid baseplate 22 preferably by hook and loop strips 28 extending along the bottom of bellows chamber 33 and the underside of bellows 133.

When inflated, bellows 133 pivotally displaces footplate 61 preferably a maximum of 30 degrees upward relative to baseplate 22. The angle of displacement can be adjusted, either by regulating the volume of air which enters and exits the bellows during each cycle, or by providing a mechanical stop, or a shielded cable limiting the degree of pivot of the footplate. For example, FIG. 7 shows adjustable stop nut 141 which can be set to limit the rotational travel of foot plate 16 with respect to base plate 22 preferably between 1 and 30 degrees.

Figure 3:
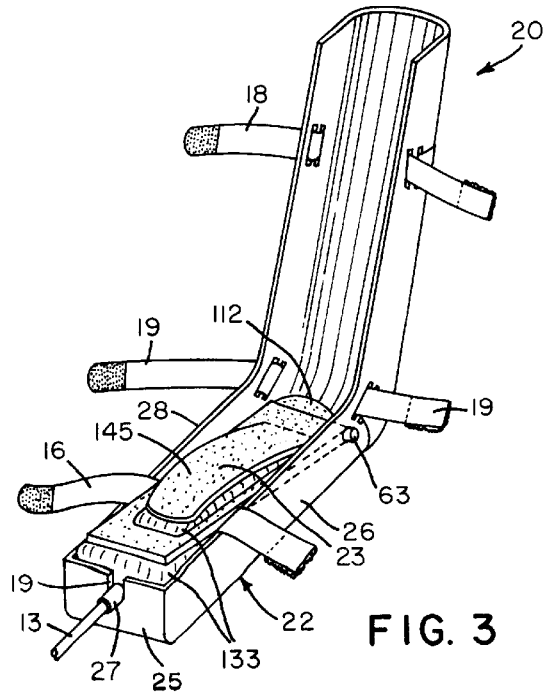
FIG. 3 is a front oblique view of an embodiment of the invention showing a base plate having a plantar opening and flexible cover.
Figure 4:
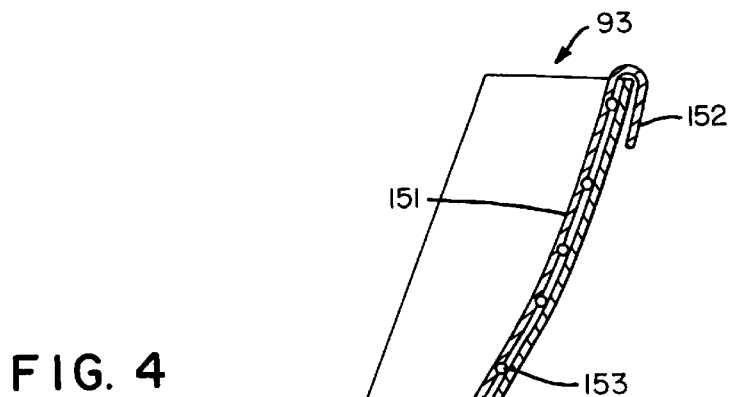
FIG. 4 is a side sectional view of a boot subsystem embodiment of the invention showing a footplate pivoted into different positions and showing a calf slide plate.
Figure 5:
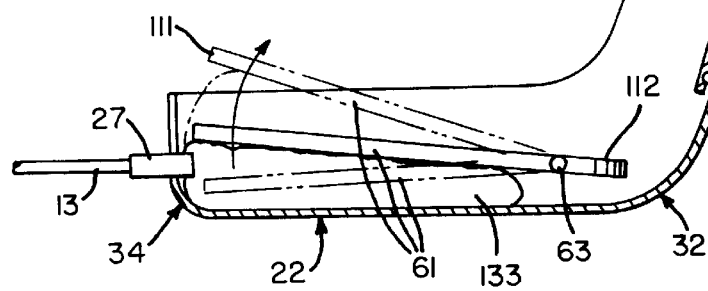
FIG. 5 is a side sectional view of an embodiment of the foot plate having a plantar opening with a roller assembly extending therethrough.

Footplate 61 is a flat or contoured plate which rotates to transmit the force of expanding bellows 133 to the foot and lower leg of a user thereby causing flexion of the foot and lower leg, and an increase in the circulation of blood and lymph therethrough. In other embodiments, footplate 61 is provided with means for effecting massage or stimilation of the plantar portion of the user's foot. For example, as shown in FIGS. 3, 5 and 6, footplate 61 is provided with plantar opening 144 which is constructed and arranged to permit a portion of bellows 133 to expand therethrough, thus delivering a massaging action to the plantar area of the foot. Stretchable footplate fabric cover 145 covers plantar opening 144 to provide a contiguous surface between footplate 61 and the user's foot. Other means of providing massaging or stimulating action to the plantar area of a user's foot also are within the scope of the invention.

For instance, as is shown in FIGS. 5 and 6, footplate 61 is provided with roller assembly 171 having rollers 173, roller assembly attachment axle 176 to connect the assembly to footplate 61. The relative movement of roller assembly 171 with respect to footplate 61 can be limited, for example, by roller assembly keeper cable 177 or by the portion of bellows 133 which can protrude through footplate 61, or by fabric web 175 which is affixed to the margins of footplate 61.

Means for limiting the travel of footplate 61 are shown also in FIG. 7 where adjustable stop 141 can be fixedly positioned in arcuate slot 142. Another means for limiting footplate travel is safety cable 143 which is attached to footplate 61 at footplate cable anchor 46 and to frontpiece 25 at frontpiece cable anchor 46. As one of skill in the art can appreciate, the length of safety cable 143 can be made adjustable. An additional means for limiting the travel of footplate 61 is that of relief valve 185 in bellows 133. Relief valve 185 can be pre-set to exhaust fluids when a particular pressure is reached, or can be made adjustable to thereby limit at bellows 133 the maximum pressure within the bellows. Connector 27 also may comprise a relief valve. Preferably, the one or more relief valves in a device according to the invention are set to open at a pressure of about 200 mm Hg.

In accordance with the construction of the invention and its interaction with the foot and leg of a user, the weight and resilience of the foot and ankle joint will place downward pressure on footplate 61 and bellows 133, thus causing return of footplate 61 to a down or neutral position when bellows 133 is deflating. However, for some users, it may be necessary to provide downward force or tension on footplate 61 to ensure its rotation downward to a down or neutral position. For instance, as is shown in FIG. 7, footplate return spring 144 is connected to footplate spring mount 149 and base plate spring mount 48 to thereby provide return tension on footplate 61.

In order to minimize irritation which may be caused in some users due to the relative movement of the user's calf with calf member 51, some preferred embodiments of the invention may be provided with hooked slide plate 151 having slide plate rollers 153 which roll on the inside of calf member 51. Preferably, hooked slide plate 151 is not affixed to calf member 51 but is instead held in close proximity thereto by slide plate hooked portion 152.

In accordance with some preferred embodiments, the invention can be actuated and deactuated manually by the user at controller 1, or by a wired or wireless remote communicator controlled by the user and in communication with controller 1. The invention can also be operated from a pre-set or adjustable timer or timer circuit provided in controller 1. Controller 1 can also be constructed and arranged to deactuate and actuate the invention in accordance with feedback from, for example, an electromyograph lead placed in the user's calf muscle or on the skin over the user's calf muscle.

Figure 8:
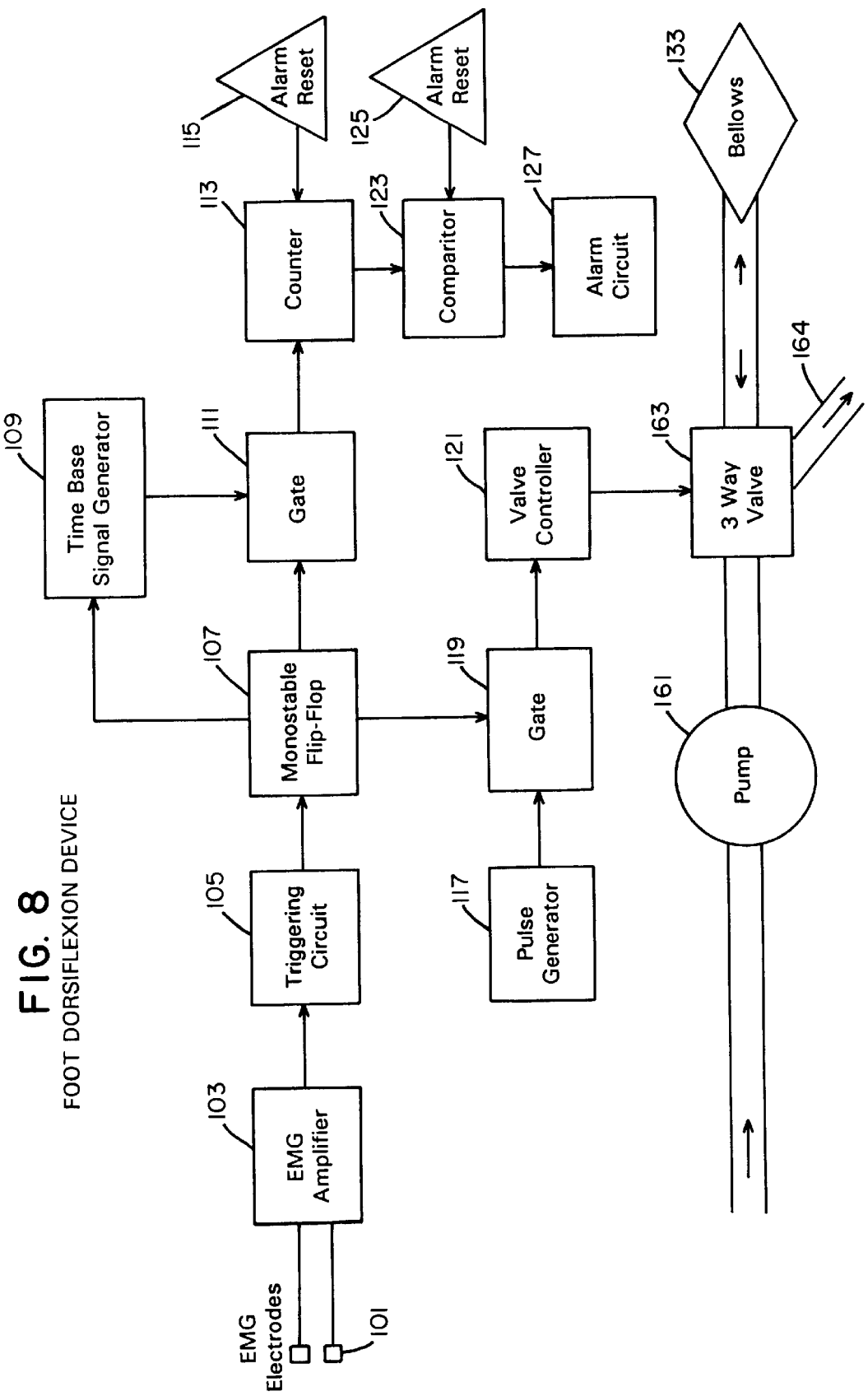
FIG. 8 is a schematic diagram of one preferred embodiment of the invention showing features useful for adjusting and controlling the actuation and deactuation of the device.
Figure 9A:
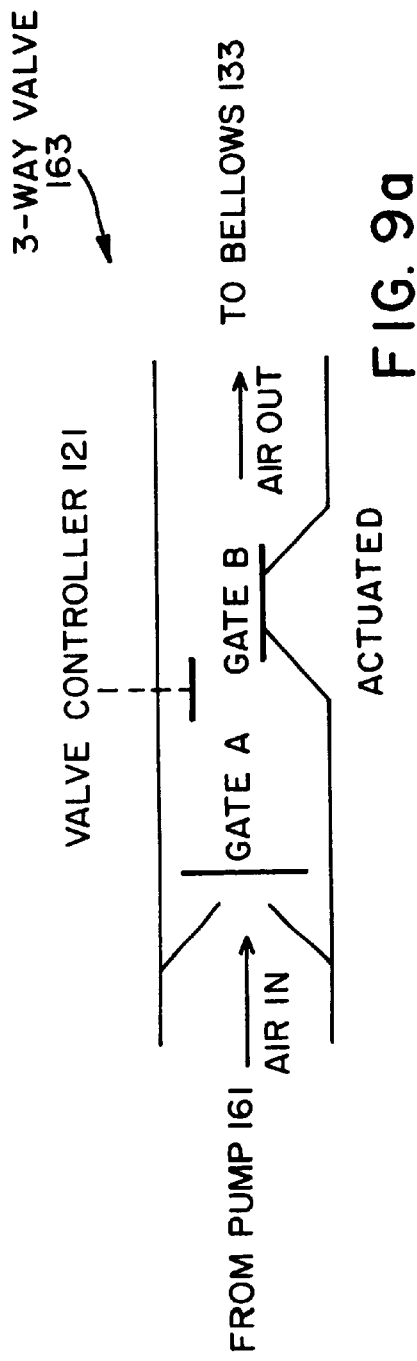
FIG. 9(a) and (b) is a schematic diagram showing operation of a threeway valve in accordance with the invention.
Figure 9B:
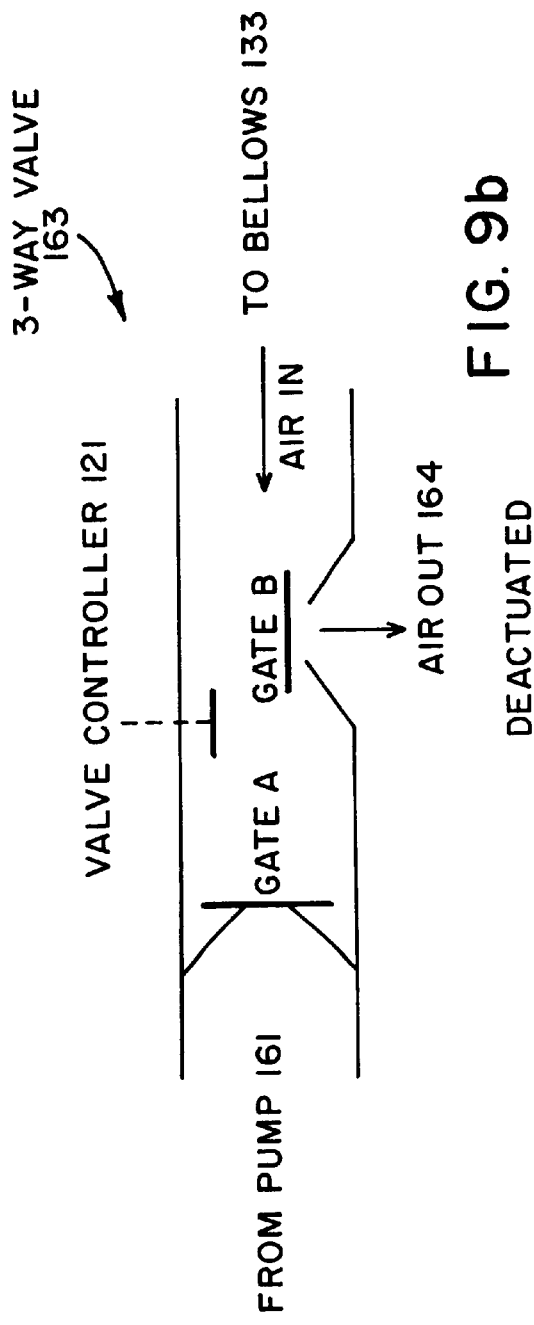

As is illustrated schematically in FIG. 8, when a device according to the invention is actuated, pump 161 pumps fluid from a fluid source, such as the atmosphere in the case of air, through three-way valve 163. Three-way valve 163, which is controlled by valve controller 121, in turn directs the fluid input from pump 161 either to bellows 133 to thereby inflate bellows 133, or to exhaust port 164 to thereby deflate bellows 133. Valve controller 121 receives pulses, typically at a rate in the range of from 1–20 /minute, from pulse generator 117 through gate 119. The frequency of output of pulse generator 119 is adjustable to thereby control the rate of cycling of the device. The device remains actuated unless it is turned off or is interrupted by a signal from monostable flip-flop circuit 107.

Pump 161 is an electrically operated pump, preferably driven by a 110 volt electrical motor so that power sources are readily available wherever the device is to be used. Other types of pumps are readily adaptable for use according to the invention, as long as their output and dependability characteristics fall within the parameters of the invention. For example, a battery-powered electrical pump would be suitable for use with the invention and render it even more convenient and portable.

In accordance with other aspects of the invention, adjustments to the fluid volume and pressure input to bellows 133 may be made to regulate the overall force applied to a user's foot. Similar adjustments to the pressure and volume input into bellows 133 may be made also to limit the extent of travel of footplate 61. Additional control of the extent of travel of footplate 61 may be provided, such as, for example, adjustable stop 141 thereby limiting the maximum degree of pivot of footplate 61 with respect to baseplate 22 and calf member 51.

In some embodiments, a device according to the invention is provided with at least one muscle activity feedback system which pauses or shuts down input into the bellows in response to a signal generated by a sensor. In accordance with some preferred embodiments of the invention, at least one electromyograph ("EMG") sensor 12 is attached to the skin of the lower leg area of a user of the device. With reference to FIG. 8, output from the EMG sensor is used to monitor the status of the musculature of the lower leg of the user. EMG sensor 12 senses electrical activity of the muscles of the lower leg and provides electrical output to EMG amplifier 103. Amplifier 103 in turn amplifies the signal received from EMG sensor 12 and provides an amplified electrical signal to triggering circuit 105. Triggering circuit 105 in turn provides a signal to monostable flip-flop circuit 107 which is in operative connection with both time base signal generator 109 and gate 111. Gate 111 in turn is in operative connection with counter 113 having alarm reset 115. Counter 113 in turn is operatively connected to both alarm circuit 127 and alarm set 125 through comparator 123.

When actuated, a device according to the invention continues a pre-set, timed inflation/deflation cycle wherein air is pumped by pump 161 through three-way valve 163 which in turn supplies air to inflate bellows 133 and provides exhaust valving to deflate bellows 133. The device remains actuated unless it is de-actuated by a signal from monostable flip-flop switch 107.

In accordance with some preferred embodiments of the invention, deactuation or "pausing" of footplate 61 occurs in response to a signal originating in EMG sensor 12. Typically, when musculature is at rest or in passive motion such as that caused by a foot flexion device, the signal detected by an EMG sensor on nearby skin or muscle is of an obscure or random nature. For example, a muscle at rest typically generates less than 50 microvolts and a muscle in active voluntary motion generates less than 500 microvolts. However, when the muscle is in spasm or tetany, the signal detected by EMG sensor 12 is of significantly greater magnitude, typically at least 1,000 microvolts and as great as 25 millivolts. Thus, when EMG sensor 12 detects a tetany spike, EMG amplifier 103 amplifies the detected signal, transmits the amplified signal to triggering circuit 105 which in turn triggers monostable flipflop circuit 107 to thereby stop the motion of footplate 61 with respect to baseplate 22.

From the foregoing, one of ordinary skill in the art will recognize how the present invention achieves all of the initially set forth objects by providing a fluid-operated foot dorsiflexion device which is both portable and easily applied and which will enhance blood flow in the lower extremities. Further, it should be appreciated how the device may be applied to unconscious users without the fear of machine-induced injury and, because the boot structure of the device is worn below the knee of a user, how the device will allow for unrestricted movement by the wearer. Moreover, because the boot structure according to the invention is preferably made of plastics and non-corroding metals such as stainless steel and titanium, it can be submersed during using in, for example, a heated therapeutic salt or oil bath, thereby increasing the therapeutic benefits it affords. Also, it should be appreciated how the preferred embodiments can be used in the hospital, home and, in future embodiments, the workplace.

Lastly, while we have shown and described the preferred embodiment of the present invention, it should be recognized that the present invention is not limited to that embodiment only, but is susceptible to numerous changes and modifications as will be known to those skilled in the art. Therefore, we do not wish to be limited to the details shown and described herein, and intend to cover all such changes and modifications as are encompassed by the scope of the appended claims.

What is claimed is:

1. A foot flexion device for use by a patient, comprising at least one boot comprising a calf member having a heel end and a knee end and constructed and arranged to support a calf portion of said patient's leg a baseplate having a heel end and a toe end, wherein said calf member and said base plate are rigidly attached to one another at said heel ends, a footplate having a footplate toe end and a footplate heel end, said footplate heel end being rotatably attached to said heel end of said baseplate so that said footplate may rotate with respect to said baseplate, an inflatable bellows positioned between said baseplate and said footplate such that inflation of said bellows causes rotation of said footplate relative to said baseplate to effect flexion of said patient's foot when said foot is disposed on said footplate, securing structure constructed and arranged to secure said patient's foot such that said footplate and foot move together, a pump assembly for pumping fluid to said bellows to power movement of said footplate, a controller operatively coupled to said pump assembly by at least one sensor constructed and arranged to sense and transmit a sensor signal from a muscle of said patient to said controller, wherein said controller is constructed and arranged to receive said signal and pause said pumping when said signal indicates that said muscle is contracting spontaneously or irregularly, and wherein said knee end of said calf member does not extend higher than the knee of said patient.

2. A foot flexion device according to claim 1, further comprising at least one switch operable by an operator or by said patient, wherein said switch is constructed and arranged to send a switch signal to said controller to override or preempt said signal from said sensor to thereby pause said pumping.

3. A foot flexion device according to claim 1, wherein said sensor signal is electrical.

4. A foot flexion device according to claim 1, wherein said electrical signal is at least 500 microvolts.

5. A foot flexion device according to claim 1, wherein two boots are provided, each boot having a bellows connected to said pump.

6. A foot flexion device according to claim 1, wherein said fluid enters and exits said bellows by means of a tube connected between said pump and said bellows.

7. A foot flexion device according to claim 1, wherein said pump assembly and said controller are connected to said boot only by said tube so that said boot is physically and electrically isolated from said said pump assembly and said controller.

8. A foot flexion device according to claim 1, wherein said at least one sensor is an electromyogram lead and wherein said controller is electrically isolated from said patient and from said boot.

9. A foot flexion device according to claim 1, wherein said controller is programed to restart from said pause following a period of electrical silence from said sensor.

10. A foot flexion device according to claim 9, wherein said electrical silence is the detection of no electrical signal greater than 100 microvolts.

11. A foot flexion device according to claim 9, wherein said controller is adjustable to restart said pumping following a period of electrical silence of from 1.0 to 5.0 minutes.

12. A foot flexion device according to claim 1, wherein said pump assembly and said controller are adjustable to inflate and deflate said bellows from 1.0–20.0 cycles/minute.

13. A foot flexion device according to claim 1, wherein said fluid comprises one or more gasses selected from the group consisting of air, nitrogen, oxygen and carbon dioxide.

14. A foot flexion device according to claim 1, wherein said fluid comprises one or more liquids selected from the group consisting of water, isotonic saline, saltwater and oil.

15. A foot flexion device according to claim 1, wherein said fluid comprises a mixture of one or more gasses selected from the group consisting of air, nitrogen, oxygen and carbon dioxide, and one or more liquids selected from the group consisting of water, isotonic saline, saltwater and oil.

16. A foot flexion device according to claim 1, further comprising a pressure release valve to prevent over-inflation.

17. A foot flexion device according to claim 1, wherein said structure constructed and arranged to secure the patient's foot to said footplate is one or more selected from the group consisting of hook and loop fasteners, straps and buckles, tensioned fabric, and at least a portion of a stocking affixed to the footplate.

18. A foot flexion device according to claim 17, wherein said means constructed and arranged to secure the patient's calf to said calf member of said boot is one or more selected from the group consisting of hook and loop fasteners, straps and buckles, tensioned fabrics, and at least a portion of a stocking affixed to the calf member.

19. A foot flexion device according to claim 1, wherein said boot is constructed and arranged to allow attachment of said boot to the footrest of a wheelchair or similar assistive device.

20. A foot flexion device according to claim 1 wherein said boot may be incorporated into a receptacle or other such housing which can be placed on the floor to allow seated patients to benefit from the device.

21. A foot flexion device according to claim 1, wherein said boot is operable while submersed in a therapeutic liquid.

22. A foot flexion device according to claim 1, wherein said therapeutic liquid is one or more selected from the group consisting of water, aqueous solutions of therapeutic substances, aqueous salt solutions and therapeutic oils.

23. A foot flexion device according to claim 1, wherein the point of rotatable attachment of said footplate heel end to said baseplate is adjustable so that said foot flexion device may be specifically fitted to said foot of said patient.

24. A foot flexion device according to claim 1, wherein said boot is provided with adjustable means constructed and arranged to effect dorsiflexion of said patient's foot within a range controllable by said adjustable means.

25. A foot flexion device according to claim 24, wherein said range is from 1 degree to 30 degrees.

26. A foot flexion device according to claim 1, wherein said controller is adjustable to operate within a range of inputs from said at least one sensor.

27. A foot flexion device according to claim 1, wherein said controller is powered by a battery and said pump is powered by alternating current provided at a voltage between 100 and 250 volts.

28. A foot flexion device according to claim 1, further comprising means for stimulating the plantar area of said foot of said patient.

29. A foot flexion device according to claim 28, wherein said means for stimulating said plantar area is constructed and arranged so that said means operates when said footplate is fixed with respect to said baseplate or when said footplate is disposed to rotate with respect to said baseplate.

30. A foot flexion device according to claim 29, wherein said means for stimulating said plantar area comprises a plantar aperture in said footplate constructed and arranged so that, during inflation, a portion of said bellows protrudes through said aperture to effect stimulation of said plantar area of said patient's foot.

31. A foot flexion device according to claim 30, wherein said plantar aperture in said footplate is provided with a roller plate so constructed and arranged that, during inflation, a portion of said bellows displaces said roller plate through said aperture to effect stimulation of said plantar area of said patient's foot.

32. A foot flexion device according to claim 1, wherein said controller can be operated by said operator by wireless remote control means.

33. A foot flexion device for use by a patient, comprising at least one boot comprising a calf member having a heel end and a knee end and constructed and arranged to support a calf portion of said patient's leg a baseplate having a heel end and a toe end, wherein said calf member and said base plate are rigidly attached to one another at said heel ends, a footplate having a footplate toe end and a footplate heel end, said footplate heel end being rotatably attached to said heel end of said baseplate so that said footplate may rotate with respect to said baseplate, an inflatable bellows positioned between said baseplate and said footplate such that inflation of said bellows causes rotation of said footplate relative to said baseplate to effect flexion of said patient's foot when said foot is disposed on said footplate, securing structure constructed and arranged to secure said patient's foot such that said footplate and foot move together, a pump assembly for pumping fluid to said bellows to power movement of said footplate, a controller operatively coupled to said pump assembly by at least one switch constructed and arranged to be operable by an operator to send a signal to said controller, wherein said controller is constructed and arranged to receive said signal and pause said pumping when said signal is received, and wherein said knee end of said calf member does not extend higher than the knee of said patient.

34. A foot flexion device according to claim 33, wherein said operator is said patient.

35. A foot flexion device according to claim 33, wherein said controller can be operated by said operator by wireless remote control means.

* * * * *